United States Patent [19]
Alt

[11] Patent Number: 5,102,403
[45] Date of Patent: Apr. 7, 1992

[54] THERAPEUTIC MEDICAL INSTRUMENT FOR INSERTION INTO BODY

[76] Inventor: Eckhard Alt, Eichendorffstrasse 52, 8012 Ottobrunn, Fed. Rep. of Germany

[21] Appl. No.: 539,153

[22] Filed: Jun. 18, 1990

[51] Int. Cl.$^5$ ............................................. A61M 25/00
[52] U.S. Cl. ...................................... 604/280; 604/96; 128/772
[58] Field of Search ................................. 604/96–101, 604/280, 264; 606/191, 194, 195; 128/207.15, 673, 675, 692, 772

[56] References Cited

U.S. PATENT DOCUMENTS 4,850,358  7/1985  Millar ................................. 128/675
4,983,167  1/1991  Sahota ................................. 604/96

Primary Examiner—C. Fred Rosenbaum
Assistant Examiner—William Lewis
Attorney, Agent, or Firm—Laurence R. Brown

[57] ABSTRACT

This invention provides a cylindrical plastic catheter of the type having a distal end portion movable over a guide wire to a treatment site such as a stenosis in the cardiovascular system, wherein the catheter shape gradually changes from a tubular configuration with a cylindrical skin defining an interior inflating lumen. The skin configuration and internal lumen changes shape gradually along the catheter length for insertion of the wire into a resident guide lumen resident only in the distal end portion without bends or kinks in the wire and retaining a generally parallel disposition to the catheter axis from which it departs to penetrate the catheter. Thus a guiding groove in the skin gradually transforms into a crescent partly surrounding the guide wire before changing into a toroidal body defining a guide wire lumen. The diameter of the catheter is thus kept constant and small with consistent axial stiffness throughout its length for supporting withdrawal and intrusion from external axial forces. The balloon mounts on the catheter body cylinder for a better, more secure seal and the axial forces along the catheter are balanced about the axis so that there is no tendency to buckle or veer with entry or withdrawal forces. By supplying a groove along the length of the catheter body to receive nested therein a parallel guide wire, the outer circumferencial dimension of the combination guide wire-catheter body may be reduced for entry into vessels of restricted size.

24 Claims, 1 Drawing Sheet

THERAPEUTIC MEDICAL INSTRUMENT FOR INSERTION INTO BODY

TECHNICAL FIELD

This invention relates to instruments and methods of therapeutic treatment of the body at internal body sites and more particularly it relates to dilatation catheters movable along coronary blood vessels upon a guide wire to position an uninflated balloon at a site for treating stenosis by subsequent inflation of the balloon, or the like.

BACKGOUND ART

The art balloon dilatation catheters for treatment of stenosis in coronary blood vessels is well developed. Representative U.S. patented art includes the following briefly discussed catheters:

G. T. Schejeldahl, et al., U.S. Pat. No. 4,413,989 Nov. 8, 1983 was concerned with long treatment periods in a balloon catheter inserted over a guide wire and thus provides for dilation without interruption of the blood supply with a lumen for bypassing blood.

A. Kuhl, U.S. Pat. No. 4,439,186 provides for pulsating pressure for expansion and contraction of the balloon to permit blood flow past the balloon.

J. J. Leary, U.S. Pat. No. 4,545,390 is concerned with steering the balloon and thus provides a steerable end to the guide wire upon which the balloon rides.

M. J. Horzewski, et al., U.S. Pat. No. 4,748,982 June 7, 1988 provides a balloon dilatation catheter with a short distal end portion moving along a guide wire with the feature of decreasing stiffness of the catheter body from the proximal extremity to the distal extremity in order to overcome difficulties in pushing prior catheters to a treatment site.

T. Bonzel, U.S. Pat. No. 4,762,129, Aug. 9, 1988 provides a stiffener wire in a separate balloon dilating lumen positioned parallel to the guide wire except at the distal end to aid in pushing the balloon to the treatment site.

There still reamin many unsolved problems in the art of treatment of a site within the body with instrumentation located in part outside the body. In the dilatation catheter art, for example, there are problems of pushing catheters into position at the treatmenmt site through restricted body vessels. Any unbalance of thrust forces or bends or kinks in te catheter can interfere with insertion or withdrawal. Critical is the friction encountered in moving a catheter along a guide wire. While considerable friction is removed by inserting the guide wire only at a distal end region of the catheter, the adds criticality by introducing a tendency to tilt or veer in the presence of slightly off axis thrust forces or unbalances of size, strength or axial stiffness of the catheter body. This is particularly evident at entrance point of the wire into the catheter body, where it is common to bend or distort the path of the guide wire, thereby adding unwanted friction and guiding problems. An example of this is given by the sharp bending zone in the guidewire set forth in the Horzewski patent.

Furthermore with dilatation balloon structure affixed to the catheter body and subjected to dilating by means of injecting fluid at high pressure, there are sealing and inflation problems. Thus, because of the high inflation pressures, any attempt to seal on a non-cylindrical surface produces a tendency to either produce leakage by tearing away the sealing joint or an uneven inflation of the balloon structure causing weak points or misshaping. Shaping is critical for passage into stenosis areas, and leakage or pressure limitations critical to the treatment and safety of the patient.

Another problems area is the abrupt transition of a catheter tubing body or lumen at transition areas for entry of a guide wire or mounting of a balloon. This can for example tend to cause damage to vesel sidewalls or as heretofore discussed by causing the short distal end rider type of catheter geneally preferable to reduce friction on insertion between the catheter and the guide wire or its connection tubing to bend, veer, buckle or bind on the guide wire in response to pushing or pulling axial forces exerted along the catheter axis to insert or withdraw the catheter.

The distal end profile of a balloon is critical particularly if it needs to be forced through a stenosis. The flexibility of the balloon for dilation is inconsistent with the initial need for penetration of restricted passageways to position the balloon at a treatment site for dilation. As a matter of fact any abrupt transition from one material to another or from one shape to another as it occurs if two separate lumens—one for inflation of the balloon and one for guidance of the wire—cause an abrupt joint between the lumens such as in the catheter suggested by Bonzel, supra, such abrupt changes provide problems of insertion, positioning and reliability.

Particularly for coronary blood vessel treatment, small diameters, known as low profile, for insertion into branch vessels and flexibility to bend around sharp corners is critical. Thus balloons attached to stiff tubings or those unadapted to bend around a vessel curve are of limited use as well as those requiring significant room resulting in greater diameters of the catheter body for mounting elements affixing the balloon structure upon the catheter.

Very critical to coronary vessel treatment is the quick interchange of dilatators of different size. Thus a smaller diameter dilatator balloon may be used for penetration of the stenosis and enlargement enough to accommodate a larger diameter balloon necessary to restore a reasonably normal working diameter in the vessel.

It is therefore a particular object of this invention to provide an improved dilatation catheter particularly adapted for angioplasty and treatment of coronary vessels that resolves the foregoing problems in the prior art.

A more general object is to provide improved instrumentation and treatment methods for therapeutic treatment at sites within the body from the outside.

Other objects, features and advantages of the invention will be found throughout the following description, and in the accompanying drawings and claims.

DISCLOSURE OF THE INVENTION

This invention provides therapeutic instrumentation and treatment methods for treatment inside the body of the type that is passed over a guide wire of positioning at the treatment site. A specific example is an inflatable dilatation catheter specially adapted for arteriosclerotic vessel treatment of stenosis or angioplasty. The catheter is of the type riding on a guide wire only at a short distal end portion. Novel features of this catheter include the transition of the catheter tubing, typically plastic having a cylindrical thin skin-like wall surrounding a single inflation lumen for dilating and accompanying balloon to accommodate a second guide wire lumen at a predetermined length of the catheter body near the distal end.

Thus the configuration of a conventional cylindrical catheter tubing with outer plastic wall defining a single internal lumen changes gradually while passing through successive configurations at the more distal (balloon) end. Thus the generally substantially cylindrical outer wall, becomes grooved to guide a substantially parallel guide wire alongside toward the interior of the catheter without any substantial bending of the wire. The catheter groove then progressively leads into a crescent shaped wall-lumina configuration which partially encompasses the guide wire before becoming cylindrical to surround the guide wire as a toroid. In parallel to this grooving and encompassing process, the inner lumen of the catheter changes its shape as well from round towards more of a C-shaped configuration. This unique and novel feature contributes significantly to smaller total diameter of dilatation catheters despite the same mechanical strength for pushing the catheter forward, compared to conventional arrangement with two parallel cylindrical lumens. The distal end lumen and body structure finally tapers into a low profile solid nose adapted for working its way through stenosis before the balloon affixed to the cylindrical length of the catheter body is placed at the stenosis. The wall of the inflating-deflating tube is apertured at the site of the balloon to connect the balloon via the inflating-deflating lumen within the catheter body to the outside of the human body for operation of the balloon by fluid injection under pressure. This provides a short low friction rider of limited length and of small diameter substantially cylindrical. This cylindrical diameter extends along the entire length of the distal catheter body that it can be introduced into smaller vessels in the coronary system for treatment.

The novel structure permits construction at the entry position of the guide wire into the catheter body at a position having a common shape and consistent still axial strength with the rest of the catheter body to facilitate feeding into a treatment site. A lateral modulus of elasticity sufficient to permit bending about sharp curves is provided within the plastic catheter body devoid of stiffener wires. The bending is enhanced around curves by the novel form of the inflating lumen as a C-shaped lumen, which bends readily as the catheter is inserted. It also readily permits withdrawal and replacement of small diameter catheters in small passageways with progressively increasing balloon sizes when needed.

When a catheter and a guide wire are inserted into an arterial vessel of sufficient size over an introducer sheet, the diameter of the dilatation catheter plus that of a guide wire lying outside the catheter is not critical to the possibility to introduce the system into the human body. But there are conditions where severely diseased and narrowed vessels make the size of the introducer sheet critical to the success of insertion. In those cases, the overall diameter of the dilation catheter and the guide wire together can be decreased if a groove is present along the entire catheter structure forwards of the outside of the body. By this means the guide wire is situatied within the circumferential groove in the dilation catheter enabling small size introducer sheets.

BRIEF DESCRIPTION OF THE DRAWINGS

Like reference characters are used to identify similar features throughout the drawings, wherein.

THE PREFERRED EMBODIMENT

Figure 1:
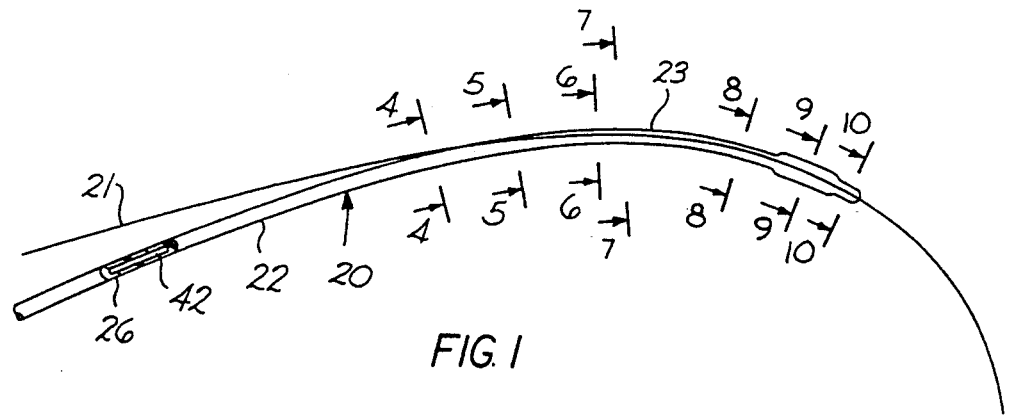
FIG. 1 is a sketch of a distal end portion of a dilatation catheter of this invention showing a low friction saddle rider portion of the catheter merging into and surrounding a substantially parallel guide wire upon which the catheter distal end rides.

In the present invention, the catheter can be given special and critical properties by means of treatment of plastic materials from which the catheter is formed. For example, silicones, polyethylenes, polyurethanes, polyvinylchlorides and like synthetic plastic materials are readily formed into desired shapes by injection molding techniques, and may be after treated by thermal molding.

The distal rider end of the catheter afforded by a preferred embodiment of this invention also is molded from a suitable plastic material to have a gradual transformation along the axial length from an initial substantially round cylindric shape to a modified shape of the dilatation fluid lumen without abrupt changes from a generally cylindrical configuration of constant diameter for penetration of a guide wire into a gradually created second guide wire lumen formed inside the catheter body. The catheter body comprises an outer body skin defining an internal cylindrical dilation fluid lumen which is gradually conformed along a predetermined portion of the length into a riding saddle over the guide wire.

Along this length, which permits the guide wire to remain along its length with a substantially parallel axis with the catheter body, the catheter body wall gradually progresses from a groove into a crescent shaped wall and internal lumen which at least partly surrounds the guide wire. The crescent closes toroidally about the guide wire to form a guide wire lumen which gradually extends toward the axis of the catheter body as the dilating lumen and outer configuration tapers into a terminal nose of solid plastic material. The generally cylindrical body shape is maintained at a constant diameter, with a cylindrical outer region positioned between the entry point of the guide wire and the nose for attachment of a circumferential dilatation balloon. Communication between the balloon and dilation fluid in the dilation lumen results from apertures in the body wall.

Throughout the transition portion of the length catheter axial stiffness is maintained constant to facilitate entry and withdrawal of the catheter. Lateral bending elasticity is provided by the material and shaping of the lumen without substantially departing from the initial cylindric shape in order to facilitate bending in conformation with body vessels.

The balloon or balloon mounting vicinity of the catheter may be radiation tempered. The C-shaped lumen may be reinforced by shaping or adding reinforcement means internal to the lumen at any points of critical stress under pressure caused by non-round lumen shaping. The tempered portions of the catheter can be treated to give a lateral bending modulus for similarly bending around curves without significant effect to the axial pushing stiffness required for positioning and withdrawing the catheter over a substantially parallel guide wire. Preferably the balloon at the distal end terminates near a solid plastic nose section tapered to provide less friction in penetrating a stenosis area for example to position the balloon for dilatation. Also preferably the balloon exterior perimeter tapers at both ends and has no disruptions.

By having a common circumferential plastic body about the dilatation lumen cavity smoothly an progressively changing along the catheter length into an interior guide wire lumen without abutments or steps in the catheter diameter, many problems of exerting distortion forces on the catheter or balloon surface for reaching treatment sites are eliminated. This all results in a more reliable, low friction, easy to insert balloon dilation catheter with a smaller diameter catheter in the region of the balloon than known in the prior art.

Figure 2:
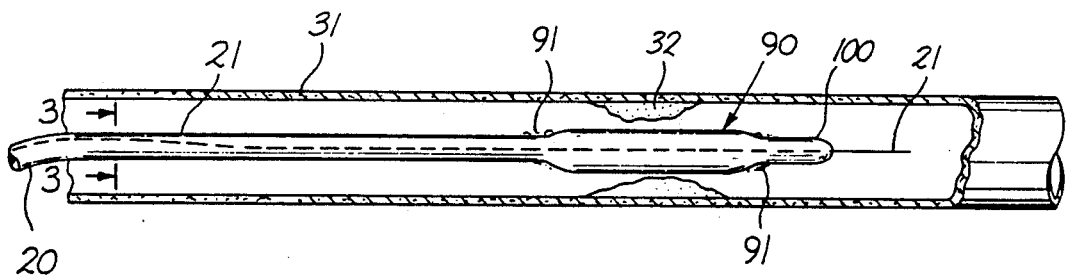
FIG. 2 is a broken away fragmental sketch of the dilatation catheter functioning at a treatment site inside a body vessel at a stenosis treatment site.
Figure 3:
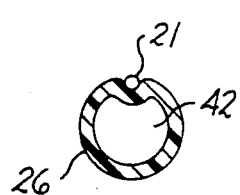
FIGS. 3 to 10 are respective cross sectioned portions of the catheter at corresponding positions 3—3, etc. shown on FIG. 1.
Figure 4:
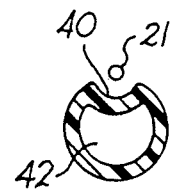
Figure 5:
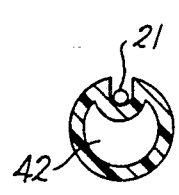
Figure 6:
Figure 7:
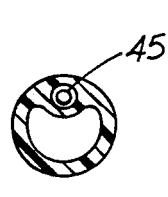
Figure 8:
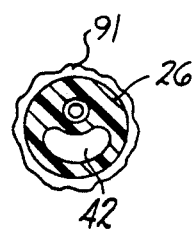
Figure 9:
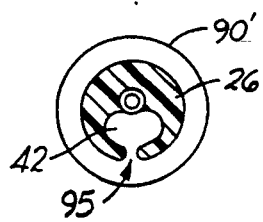

As may be seen in FIGS. 1 and 2, the catheter of this invention is ideally suited for treament of cardiac disease such as stenosis 32 of arterial vessel wall 31. The catheter 20 is inserted into the cardiovascular system typified by vessel 31 over a previously inserted guide wire 21 which runs parallel outside the catheter until it reaches a distal end region 23 for guiding the catheter to carry instrumentation such as a dilatation balloon located near its distal end to a treatment site 32.

This catheter is of the type that as it nears the distal end 23, the guide wire 21 is gradually more and more encompassed and thus little friction between the guide wire and catheter is present to impede insertion or withdrawal of the catheter from a position outside the body. The catheter at region 2—2 of this embodiment is generally of cylindrical shape having an internal inflation lumen 42 for fluid under pressure to expand a dilatation balloon in the distal end region 22. The catheter body is formed of a plastic material 26 having enough axial stiffness to push the distal end 23 over the guide wire 21 and through small or stenosis restricted cardiovascular blood vessels into a treatment site without buckling or restricting the lumen 42 diameter, as aforesaid.

Figure 10:
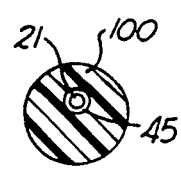

The catheter throughout the distal end regions 4—4 to 10—10, as shown in cross section in corresponding FIG. 4 through 10, undergoes smoothly progressing changes of shape of the wall 26 and lumen 42. The distal terminal end at FIG. 10 is of solid plastic which tapers to a penetration shape, which helps to advance the balloon more easily over an already positioned guide wire through high degree narrowings so that the balloon section of FIG. 9 may be placed into position for dilatation as shown in FIG. 2 within the blood vessel 31 at stenosis site 32. The guide wire facilitates withdrawal of the catheter 20 along the guide wire 21 and allows its replacement with one having a larger diameter head end portion allowing a greater degree of dilatation. Because of the easy insertion of the guide wire into the novel guiding lanes and of the limited length of guidance of the wire in the balloon possible with this invention, initial treatment with a smaller balloon can readily be followed by a subsequent treatment with a larger balloon without the need for extensive guiding of the new catheter over a guide wire of more than double the length of the catheter.

The smoothly changing shape of the catheter along its axial length at the balloon site critical to this invention allows for an exchange of catheters without significant friction thus facilitating easy and fast pull back and advance of subsequent catheter structure over a guide wire. This can be visualized as related to the cross sections of FIGS. 3 to 10. Thus the catheter plastic body wall 26 becomes more deeply grooved at 40 for guiding the guide wire toward its final position, in this embodiment coaxial with the balloon as shown in FIG. 10. Thus guide wire 21 enters the catheter body axially from left to right (FIG. 1) through a groove, a crescent shaped semi-enveloping configuration, FIGS. 5 and 6, and then completely surrounded as in FIGS. 7 through 10. Thus the catheter is transformed from a single lumen catheter into two lumens, adding one for the guide wire, all without changing substantially the outer cylindrical body configuration or its diameter. Furthermore, the guide wire gradually enters its new guiding lumen through several changes of guidance within a groove, and thus incurs no kinking or sharp bending as mandatory for low friction removal or advance of the catheter over the guide wire.

Also the lumen shape changes gradually within the catheter 20 as seen through the progression of FIGS. 3 to 9, for this embodiment. Note that the balloon 90 has an outer skin 91 which is distendable in the presence of fluid in the inflating lumen 42 under increased pressure into an expanded diameter 90 shown in phantom view. This balloon is affixed to the outer cylindrical catheter surface at each end. That is critical in that high internal pressures are minimized and equalized about the joint, resulting in more reliability and operation at greater safety margins.

The small diameter of the catheter 20, especially at zone 23, permits good lateral flexibility to bend around curves in the cardiovascular vessels. At the tip 100, a special material with some pliability is preferred for use in penetration of a stenosis region and this may be achieved by thermal or radiation treatment.

The smooth progressive change of shape of the catheter body 26 and its internal inflating lumen 25 to convert the single lumen catheter to one having an additional internal guide wire lumen 45 without substantially changing the direction of travel of the guide wire and the constant outer catheter diameter throughout is typified by the sequence in the FIGS. 3 to 10. Thus the catheter body 26 of FIG. 3 becomes grooved at FIG. 4, with the body 26 and internal lumen 42 becoming crescent shaped at FIGS. 4 and 5. The internal lumen 415 is formed at FIG. 7 so that the balloon 90 may be glued or otherwise affixed to the outer cylindrical periphery of the catheter body 26 at 91 in FIGS. 2 and 8. The aperture 95 in the catheter body 26 of FIG. 9 permits balloon 90 to be dilated from fluid in lumen 42 to the inflated balloon condition 90. The lumen 42 is tapered toward the nose 100 shown in FIG. 10 to provide a low profile solid penetrating probe end. During this entire transition, the catheter maintains its cylindrical shape and diameter.

Accordingly it is seen heretofore and in the appended claims that this invention has advanced the state of the art with those novel features defined in the claims for examplifying the nature and spirit of the invention.

I claim:

1. A catheter with distal end structure for forming a lumen to encompass and ride along a guide wire comprising in combination:

a substantially cylindrical catheter body with an outer wall about a first lumen with the outer wall gradually changing in shape along the catheter body length toward the distal end from an entrance groove shaped as a path for guiding the wire inwardly into the cylindrical body along the catheter length to form initially a crescent shaped catheter body configuration partly surrounding the wire and which thereafter changes into a closed cylinder wall surrounding a second guide lumen for encompassing the guide wire.

2. The catheter distal end structure of claim 1 wherein the outer wall of the catheter body over the length in which the catheter changes gradually and smoothly from a single lumen configuration to a two lumen configuration is substantially cylindrical in shape forming with the accompanying guide wire an extension of the cylindrical catheter body.

3. The catheter distal end structure of claim 1 wherein the path of the wire through the groove and crescent shaped configuration into the second quide lumen is substantially parallel with the catheter body.

4. The catheter distal end structure of claim 1 wherein the catheter body consists of a plastic material having a substantially constant axial stiffness throughout the distal end structure length corresponding substantially to that of the cylindrical catheter body, for permitting the catheter to be inserted into or withdrawn from body vessels of small dimension from a position outside the body.

5. The catheter structure of claim 1 wherein the catheter body along the length of the change from one to two lumens thereby presenting the initial lumen in a crescent shape is reinforced to prevent the generally cylindrical catheter body from distorting in shape in response to internal fluid pressures used for dilatation.

6. The catheter of claim 1 having a distal end portion formed with a substantially cylindrical outer wall along a predetermined length to which a balloon dilatation structure is affixed at two spaced positions along the cylindrical outer wall for dilation by means of fluid under pressure in the initial lumen.

7. The catheter of claim 6 wherein the dilatation balloon structure when dilated under fluid pressure has a cylindrical configuration tapering gradually down to the catheter body at two ends.

8. The catheter of claim 1 with a body consisting of plastic having a characteristic of axial stiffness and a shear characteristic permitting the catheter body to readily bend around curves.

9. A substantially cylindrical catheter body structure adapted to receive, direct, and envelop a substantially parallel disposed guide wire along a portion of the catheter's length thereby forming an internal catheter guide wire lumen by changes of shape of the cylindrical catheter body gradually over said length from a guide wire entry groove indented on the catheter outer surface into the internal lumen encompassing the guide wire.

10. The catheter structure of claim 9 wherein the catheter body shape configuration about the lumen is constructed to preserve a substantially constant longitudinal stiffness along the catheter body.

11. A therapeutic medical instrument for insertion into the body for treatment at an internal body site, comprising in combination:
guide wire means for insertion into the body to a treatment site for guiding therapeutic means thereover into the treatment site;
treatment means for insertion into the treatment site having a proximal end for employment outside the body including treatment lumen structure providing a communication path from outside the body to the treatment site, guide wire lumen structure within said treatment means for movement of the instrument along the guide wire to a treatment site, and a distal end instrument for movement inside the body to a treatment site;
treatment means structure for inserting the guide wire means into the guide wire lumen confined to a short length low friction coupling region near the distal end of the treatment means at a linear portion having a substantially cylindrical body of substantially constant diameter, whereat the treatment lumen configuration changes in shape gradually along said coupling region to receive the guide wire and fully encompass the guide wire, and
wherein the coupling region structure in the instrument for introducing the guide wire into the guide wire lumen without substantial change of direction of the guide wire from a parallel position alongside the treatment means body providing a smooth progressive transition from cylindrical shape, to indented cylindrical shape provides a groove for guiding the guide wire, to substantially cresent shape for partly surrounding the wire, to the guide lumen.

12. A catheter for use with a companion guide wire having means for retention of the guide wire substantially within the catheter outer perimeter for insertion into a body vessel of restricted size, comprising in combination, a catheter body having a longitudinal groove internally indented in the outer periphery along a portion of the catheter length adapted to nest a guide wire therein and structure gradually changing the groove into a lumen within the catheter body for retaining the guide wire to thus produce a reduced outer perimeter for the catheter and guide wire.

13. A catheter as defined in claim 12 having a guide wire nested in said groove thereby producing a substantially cylindrical outer perimeter of the combined catheter body and guide wire.

14. A combination of a guide wire and catheter adapted for insertion into a body vessel comprising in combination, a catheter body having a longitudinal groove along a predetermined length of the catheter near its distal end to be inserted into a body vessel of restricted size, said groove having a shape for receiving nested therein alongside the catheter body a substantially parallel guide wire, said groove changing into a lumen within the catheter for thereby receiving and surrounding the guide wire thereby to reduce an outer peripheral dimension of the catheter body-guide wire combination residing within the vessel.

15. The method of inserting a guide wire into the distal end of a catheter so that the catheter may ride along the guide wire with low friction comprising the steps of:
producing a hollow cylindrical catheter with a circumferential wall surrounding a lumen,
gradually changing the circumferential wall configuration to provide structure for inserting the guide wire to structurally change the circumferential wall along its length into a second lumen formed within the catheter with the initial cylindrical hollow catheter circumferential wall changing along its length to form (a) an entrance groove for guiding the wire into a crescent shaped wall section partly surrounding the wire and (b) transition structure closing the cresent to produce a guiding lumen about the wire, and
inserting a guide wire disposed substantially parallel with the catheter into the groove to follow the transition structure and enter the guiding lumen without departing substantially from the parallel disposition of the guide wire and catheter.

16. The method of introducing a guide wire into a substantially cylindrical catheter body near its distal end while maintaining the diameter of the cylindrical catheter body substantially constant along its length to a position disposed around a guiding wire in a distal end region having a dilatation balloon structure positioned circumferentially about the catheter body perimeter, comprising the steps of:
indenting the cylindrical catheter body to provide a shaped groove along the length of the body for entry of the guiding wire, changing the groove in shape along said length into a lumen surrounding the guide wire without a substantial change in diameter of the catheter body, and
inserting a guide wire disposed substantially parallel to the catheter body gradually into the dilatation catheter body along its length to dispose the guide wire substantially concentrically within the balloon without substantially changing the diameter of the catheter body.

17. The method of claim 16 further comprising the step of changing an internal dilation lument shape initially disposed within the cylindrical catheter body from substantially circular to a non-round shape to accommodate the groove for insertion of the guide wire.

18. The method of transforming a distal end of a substantially cylindrical catheter body having an internal lumen to produce an additional internal guide wire lumen therein by the steps of retaining the cylindrical body outer peripheral dimension substantially constant along its length and changing the shape of said cylindrical body and internal lumen along the length of the body to form an indented guide groove on the catheter body outer surface thereby changing the shape of the internal lumen and changing the cylindrical body shape over the length of the catheter body from the groove into said internal guide wire lumen.

19. The method of creating in a substantially cylindrical plastic catheter body, having internal lumen means, a structure for encompassing and riding over a guide wire comprising the steps of modifying the outer peripheral shape of the catheter body while substantially retaining its cylindrical configuration into an indented groove for gradually enveloping the guide wire along a predetermined length of the catheter body to produce a further internal lumen within the cylindrical body to fully surround the guide wire.

20. The method of claim 19 including the step of tapering the lumen means and the cylindrical body gradually along a distal end length of the catheter body beyond said predetermined length.

21. The method of claim 19 including the steps of affixing a dilatation balloon structure over a length of the cylindrical body behind said predetermined length having a substantially constant diameter and producing aperture means to communicate with said lumen means for dilation of the balloon structure.

22. The method of inserting into and withdrawing from a treatment site a catheter consisting of a plastic material comprising a dilatation balloon assembly having a dilating lumen and structure for riding concentrically about a guide wire along a portion of its length at a distal end position of the catheter, comprising the steps of: inserting into the treatment site a guide wire, positioning a distal end portion of the catheter substantially parallel to the guide wire, merging the external substantially parallel guide wire into a groove in an outer catheter surface portion near the distal end gradually changing into an internal lumen positioned within the catheter along a predetermined portion of the catheter surrounding the guide wire without substantially bending the guide wire, forming a catheter body over its length having a similar axial stiffness and catheter peripheral shape so that the catheter movement forces are substantially axially balanced along the body of the catheter throughout its length, and imposing both insertion and withdrawal forces at a proximal end of the catheter in a direction along the length of the catheter for inserting and withdrawing the catheter from the treatment site.

23. The method of claim 22 further comprising the step of grooving the outer periphery of the catheter along a portion of its length to conform with and receive nested therein said guided wire with the catheter body substantially constant in diameter over a merge area between the groove and internal lumen.

24. The method of decreasing the overall volume required for the combination of a catheter body and a parallel guide wire for insertion into a restricted size body tubing such as a cardiovascular vessel for treatment comprising the steps of providing a longitudinal groove along a portion of the length of the catheter body conformed with the guide wire dimensions changing the groove gradually into a lumen within the catheter body surrounding the guide wire, and feeding the guide wire and catheter into the body with the guide wire resting in the lumen.

* * * * *